United States Patent
Nadakuditi et al.

(10) Patent No.: US 9,207,171 B2
(45) Date of Patent: Dec. 8, 2015

(54) METHODS FOR INCREASING TRANSMISSION THROUGH SCATTERING RANDOM MEDIA

(71) Applicant: THE REGENTS OF THE UNIVERSITY OF MICHIGAN, Ann Arbor, MI (US)

(72) Inventors: Raj R. Nadakuditi, Ann Arbor, MI (US); Stephen C. Rand, Ann Arbor, MI (US); Eric Michielssen, Ann Arbor, MI (US); Curtis Jin, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/620,411

(22) Filed: Feb. 12, 2015

(65) Prior Publication Data
US 2015/0285739 A1  Oct. 8, 2015

Related U.S. Application Data

(60) Provisional application No. 61/938,915, filed on Feb. 12, 2014.

(51) Int. Cl.
*G01N 21/55* (2014.01)
*G01N 21/49* (2006.01)
*G01N 21/47* (2006.01)

(52) U.S. Cl.
CPC ........ *G01N 21/49* (2013.01); *G01N 2021/4735* (2013.01)

(58) Field of Classification Search
CPC ........... G01B 9/02039; G01B 9/02038; G01B 9/02024; G01N 21/47
USPC ................ 356/445–448, 512, 521, 484, 494; 250/459.1, 252.1, 458.1; 348/231.6, 79
See application file for complete search history.

(56) References Cited

U.S. PATENT DOCUMENTS

| | | | | |
|---|---|---|---|---|
| 2012/0018614 A1* | 1/2012 | King | ...................... | G02B 26/06 250/201.9 |
| 2013/0015367 A1* | 1/2013 | Cui | ........................ | G02B 26/06 250/459.1 |
| 2015/0036021 A1* | 2/2015 | Gigan | ................... | G06T 11/006 348/231.6 |

OTHER PUBLICATIONS

Curtis Jin et al., "Iterative, Backscatter-analysis Algorithms for Increasing Transmission and Focusing Light Through Highly Scattering Random Media", J. Opt. Soc. Am. A, vol. 30, No. 8 dated Aug. 2013.

*Primary Examiner* — Hoa Pham
(74) *Attorney, Agent, or Firm* — Marshall, Gerstein & Borun LLP; Randall G. Rueth

(57) ABSTRACT

The method, system, and computer-readable medium increase transmission of waves through a highly scattering random medium. Transmission is increased by iteratively refining wavefronts using measurements of the backscatter wavefronts resulting from transmission of waves into the medium. The process of double phase conjugation by time-reversing a wavefront, transmitting the time-reversed wavefront into the medium, and time-reversing the reversing backscatter wavefront is leveraged to implement the method in a physical system using a phase conjugate mirror. In an embodiment, transmission may be increased by phase-only modulation of the wavefronts. In an embodiment, the invention may be used to focus transmission through the medium to a location opposite the wave source.

20 Claims, 2 Drawing Sheets

METHODS FOR INCREASING TRANSMISSION THROUGH SCATTERING RANDOM MEDIA

CROSS-REFERENCE TO RELATED APPLICATIONS

This application claims the benefit of U.S. Provisional Application No. 61/938,915, filed Feb. 12, 2014, the entirety of which is incorporated by reference herein.

GOVERNMENT RIGHTS

This invention was made with government support under Grant No. CCF-1116115 from the United States National Science Foundation, Office of Naval Research Young Investigator Award N00041110660, and Grants No. FA9550-12-1-0266 and FA9550-12-0016 from the United States Air Force Office of Scientific Research. The government has certain rights in the invention.

TECHNICAL FIELD

The invention relates generally to methods and devices for signal transmission and, more particularly, to methods and devices for transmitting waves through highly scattering random media.

BACKGROUND

Transparent media such as glass and air are transparent because light propagates through them without being scattered or absorbed. In contrast, opaque materials prevent transmission of light by absorption or scattering. Highly scattering random media such as biological tissue, turbid water, white paint, and egg shells are opaque because they contain randomly arranged particles, which cause light to scatter in many directions. This scattering effect becomes more pronounced as the thickness of the highly scattering random medium increases, and less and less normally incident light is transmitted through the medium. Scattering thus severely curtails the usefulness of optical techniques for sensing and imaging in highly scattering random media.

Previous work in the field has shown the existence of eigen-wavefronts that dramatically increase the transmission of electromagnetic signals in highly scattering random media (viz., wavefronts with transmission coefficients close to 1). By measuring the scattering of light that has passed through a highly scattering random medium, such eigen-wavefronts can be determined. For a given highly scattering random medium, an optimal wavefront that maximizes transmission through the medium can be produced from the eigen-wavefronts. Existing coordinate descent methods for determining such optimal wavefronts suffer from two main problems that limit the use of such methods in many applications. First, existing methods require measurement within or on the far side of the medium from the source of the signal. Second, existing methods converge to an optimal wavefront slowly. Existing coordinate descent methods maximize the measured intensity of each mode of a transmitted wavefront while holding the amplitudes and phases of all other modes constant. The process must then be repeated for each of M modes, requiring on the order of M measurements. Other existing methods use multiple frequencies to find the optimal phases simultaneously, but these other methods still require measurement through the medium and have only been shown to work for small numbers of modes.

SUMMARY

Disclosed is a method, system, and computer-readable medium storing instructions for increasing transmission of a wavefront through a highly scattering random medium using measurements of the backscatter field produced by wavefronts incident upon the medium. One embodiment consists of a computer-implemented method including refining a test wavefront in one or more iterations to produce a high-transmission wavefront, terminating the iterative refinement upon reaching a numerically prespecified level of transmission, determining a modified wavefront to transmit through the medium, and transmitting the modified wavefront through the medium. Another embodiment consists of a system including a processor, a spatial light modulator configured to modulate the wavefront and transmit the modulated wavefront into the medium, a detector configured to measure the backscatter field resulting from the transmission of the wavefront into the medium, and a program memory storing executable instructions that when executed by the one or more processors cause the system to refine the wavefront in one or more iterations, terminate the iterative refinement upon reaching a numerically prespecified level of transmission, modify the wavefront based upon the final test wavefront, and transmit the modified wavefront through the medium. Another embodiment consists of a tangible, non-transitory computer-readable medium storing instructions that when executed by one or more processors of a computer system cause the computer system to refine the wavefront in one or more iterations, terminate the iterative refinement upon reaching a numerically prespecified level of transmission, modify the wavefront based upon the final test wavefront, and transmit the modified wavefront through the medium.

The iterative refinement of the wavefront includes transmitting a wavefront into the medium, receiving a measurement of the back-scatter, determining whether the level of transmission through the medium has reached a numerically prespecified level to terminate the iterative refinement, and refining the wavefront for transmission into the medium in the next iteration. In an embodiment, the iterative refinement of the wavefront may consist of transmitting a first test wavefront into the medium, receiving a measurement of the first backscatter wavefront resulting from the first test wavefront, time-reversing the first backscatter wavefront to obtain a second test wavefront, transmitting the second test wavefront into the medium, receiving a measurement of the second backscatter wavefront resulting from the first test wavefront, time-reversing the second backscatter wavefront to obtain a third test wavefront, determining whether the level of transmission through the medium of the third test wavefront has reached a numerically prespecified level to terminate the iterative refinement, and refining the wavefront for transmission into the medium in the next iteration using the third test wavefront. In some embodiments, a phase conjugate mirror is used to time-reversing the first and second backscatter wavefronts. In an embodiment, the second test wavefront may be determined using only the phase of the modal coefficients of the first backscatter wavefront. Some embodiments may use phase and amplitude modulation of the wavefronts or may use phase-only modulation.

Refining the test wavefront in each iteration may involve adjusting the test wavefront in proportion to the third test wavefront. Refining the test wavefront may also involve adjusting the test wavefront in proportion to the average magnitude of the modal coefficients of the first backscatter wavefront. Refining the test wavefront may also involved adjusting the phase of the test wavefront in proportion to the average magnitude of the modal coefficients of the first backscatter wavefront. In an embodiment, refining the test wavefront may further comprise determining a residual vector using the third test wavefront.

In an embodiment, the refinement may include determining a matrix H using the first and third test wavefronts and a matrix Q, the columns of which are the modal coefficient vectors of the test wavefronts of each of the one or more iterations. The eigenvectors of the matrix H and the matrix Q may be used to modify the wavefront to focus the wavefront through the medium.

BRIEF DESCRIPTION OF THE DRAWINGS

The figures described below depict various aspects of the applications, methods, and systems disclosed herein. It should be understood that each figure depicts an embodiment of a particular aspect of the disclosed applications, systems and methods, and that each of the figures is intended to accord with a possible embodiment thereof. Furthermore, wherever possible, the following description refers to the reference numerals included in the following figures, in which features depicted in multiple figures are designated with consistent reference numerals.

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112(f).

Although the description within this application discusses transmission in terms of light or optics, it should be understood that these terms are used for convenience and brevity.

The method and system apply equally to any electromagnetic, acoustic, optical, or other waves propagating through a highly scattering random medium. As used herein, the term "highly scattering random medium" means any medium that has a low transmission coefficient to most waves in the applicable range of frequencies, that causes a high degree of scattering within the medium in the applicable range of frequencies, and that has a low degree of absorption within the medium in the applicable range of frequencies. The applicable range of frequencies may depend upon the particular application to which the described method or system is applied. As used herein, the term "medium" refers to a transmission medium. As used herein the superscripts $H$ and $*$ applied to a matrix or vector (e.g., $X^H$ or $X^*$) denote the complex conjugate transpose and the complex conjugate, respectively, of the matrix or vector to which they refer.

Transmission in Highly Scattering Random Media

Figure 1:
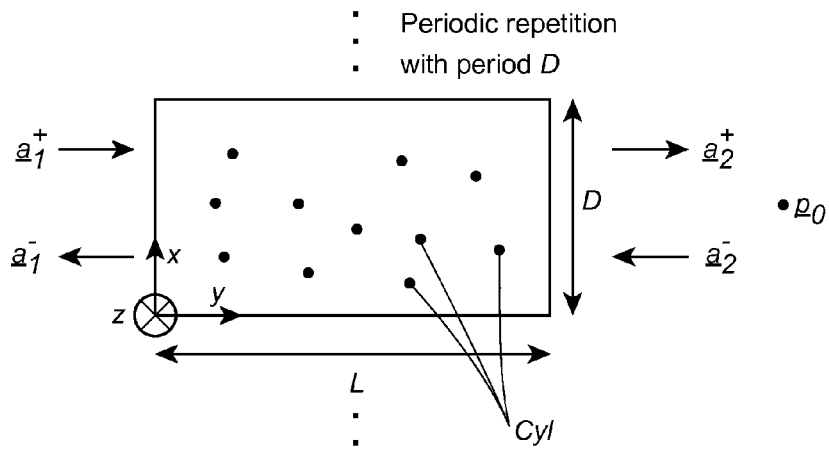
FIG. 1 illustrates an example highly scattering random medium.

FIG. 1 illustrates an example highly scattering random medium 100 as a two-dimensional periodic slab of thickness L and periodicity D. The slab's unit cell occupies the space $0 \leq x < D$ and $0 \leq y < L$ and contains N, infinite and z-invariant circular cylinders Cyl that are placed randomly within the cell. The circular cylinders may be either perfect electrically conducting or dielectric with refractive index $n_d$. In the example medium, the cylinders do not overlap and all fields are $TM_z$ polarized. Electric fields in the halfspace where y<0 (i=1) and the halfspace where y>L (i=2) are denoted as $e_i(\rho) = e_i(\rho)\hat{z}$. These fields' complex amplitudes $e_i(\rho)$ can be decomposed in terms of propagating in the +y and −y directions as $e_i(\rho) = e_i^+(\rho) + e_i^-(\rho)$, where $$e_i^\pm(\rho) = \sum_{n=-N}^{N} h_n a_{i,n}^\pm e^{-jk_n^\pm \cdot \rho}. \qquad \text{Equation 1}$$

The components of Equation 1 above are defined as follows: $\rho = x\hat{x} + y\hat{y} \equiv (x,y)$, $k_n^\pm = k_{n,x}\hat{x} \pm k_{n,y}\hat{y} \equiv (k_{n,x}, \pm k_{n,y})$, $k_{n,x} = 2\pi n/D$, $k_{n,y} = 2\pi\sqrt{(1/\lambda)^2 - (n/D)^2}$, $\lambda$ is the wavelength, and $h_n = \sqrt{\|k_n^\pm\|_2 / k_{n,y}}$ is a power-normalizing coefficient. It is assumed that $N = [D/\lambda]$, so only propagating waves are modeled. The number of modes of propagating waves is denoted as $M = 2N+1$, and the modal coefficients are denoted $a_{i,n}^\pm$ where i=1, 2 and n=−N, . . . , 0, . . . , N. Vectors of the modal coefficients are denoted $a_i^\pm = [a_{i,-N}^\pm \ldots a_{i,0}^\pm \ldots a_{i,N}^\pm]^T$ where T denotes transposition. The modal coefficients $a_{i,n}^+$ are related by the scattering matrix S as follows:

$$\begin{bmatrix} \underline{a}_1^- \\ \underline{a}_2^+ \end{bmatrix} = \underbrace{\begin{bmatrix} S_{11} & S_{12} \\ S_{21} & S_{22} \end{bmatrix}}_{=:S} \begin{bmatrix} \underline{a}_1^+ \\ \underline{a}_2^- \end{bmatrix}, \qquad \text{Equation 2}$$

For the present disclosure, the highly scattering random medium 100 is excited only from the direction of y<0; hence, $\underline{a}_2^- = 0$ and $S_{12}$ and $S_{22}$ may be disregarded. Thus, the modal coefficients of the backscatter wavefront are $\underline{a}_1^- = S_{11} \cdot \underline{a}_1^+$, and the modal coefficients of the transmitted wavefront are $\underline{a}_2^+ = S_{21} \cdot \underline{a}_1^+$. For any incident field amplitude $e_1^+(\rho)$, the transmission coefficient may be defined as $$\tau(\underline{a}_1^+) := \frac{\|S_{21} \cdot \underline{a}_1^+\|_2^2}{\|\underline{a}_1^+\|_2^2}, \quad \text{Equation 3}$$

and the reflection coefficient may be defined as $$\Gamma(\underline{a}_1^+) := \frac{\|S_{11} \cdot \underline{a}_1^+\|_2^2}{\|\underline{a}_1^+\|_2^2}, \quad \text{Equation 4}$$

The transmission coefficient of a normally incident wavefront may be denoted by $\tau_{normal} = \tau([0 \ldots 0\ 1\ 0 \ldots 0]^T)$.

From the foregoing, it can be seen that the maximum transmission of power through a highly scattering random medium 100 may be obtained by designing an optimal wavefront $\underline{a}_{opt}$ incident to the highly scattering random medium 100. The optimal wavefront $\underline{a}_{opt}$ is a wavefront for which the transmission coefficient obtains its maximum value in a system with scattering matrix S. As such, the optimal wavefront may be determined as follows:

$$\begin{aligned} a_{opt} &= \operatorname*{argmax}_{\underline{a}_1^+} \tau(\underline{a}_1^+) \\ &= \operatorname*{argmax}_{\underline{a}_1^+} \frac{\|S_{21} \cdot \underline{a}_1^+\|_2^2}{\|\underline{a}_1^+\|_2^2} \\ &= \operatorname*{argmax}_{\|\underline{a}_1^+\|_2=1} \|S_{21} \cdot \underline{a}_1^+\|_2^2, \end{aligned} \quad \text{Equation 5}$$

where $\|\underline{a}_1^+\|_2=1$ represents the incident power constraint.

The highly scattering random medium 100 can be approximated by a lossless medium. In a lossless medium, the scattering matrix S will be unitary; i.e. $S^H \cdot S = I$ where I is the identity matrix. Consequently, $S_{11}^H \cdot S_{11} + S_{21}^H \cdot S_{21} = I$, and the optimal wavefront may also be determined as follows:

$$\begin{aligned} a_{opt} &= \operatorname*{argmax}_{\|\underline{a}_1^+\|_2=1} (\underline{a}_1^+)^H \cdot S_{21}^H \cdot S_{21} \cdot \underline{a}_1^+ \\ &\quad =(\underline{a}_1^+)^H \cdot (I \cdot S_{11}^H \cdot S_{11}) \cdot \underline{a}_1^+ \\ &= \operatorname*{argmax}_{\|\underline{a}_1^+\|_2=1} \|S_{11} \cdot \underline{a}_1^+\|_2^2 \\ &= \operatorname*{argmax}_{\underline{a}_1^+} \Gamma(\underline{a}_1^+). \end{aligned} \quad \text{Equation 6}$$

In a lossless medium, the wavefront that minimizes backscattering also maximizes transmission. The same is true in a highly random scattering medium because it approximates a lossless medium. The present invention uses this equivalence to develop a method and system of maximizing transmission by minimizing backscatter, which enables the determination of the optimal wavefront $\underline{a}_{opt}$ using only the backscatter wavefront with modal coefficient vector $\underline{a}_1^-$.

Additionally, or alternatively, the optimal wavefront $\underline{a}_{opt}$ may be determined using phase modulation without amplitude modulation. Such an approach is of particular benefit in applications where amplitude modulation may be impractical, such as applications in the optical range, but the technique may be applied more generally. The modal coefficient vector $\underline{a}_1^+$ can be separated into amplitude and phase components, where $|a_{1,n}^+|$ and $\angle a_{1,n}^+$ denote the magnitude and phase of modal coefficient $a_{1,n}^+ = |a_{1,n}^+| \exp(j\angle a_{1,n}^+)$, respectively. The phase-only modal coefficient vector may then be defined as $\angle \underline{a}_1^+ = [\angle a_{1,-N}^+ \ldots \angle a_{1,0}^+ \ldots \angle a_{1,N}^+]^T$. A set $P_c^M$ may be defined comprising phase vectors each with M elements and non-zero positive real-valued constant c of the form $$\underline{p}(\underline{\theta}; c) = \sqrt{\frac{c}{M}} [e^{j\theta_{-N}} \ldots e^{j\theta_0} \ldots e^{j\theta_N}]^T, \quad \text{Equation 7}$$

where $\underline{\theta} = [\theta_{-N} \ldots \theta_0 \ldots \theta_N]^T$ is an M-vector of phases. With the incident power constraint $\|\underline{a}_1^+\|_2 = 1$ as above, the optimal wavefront $\underline{a}_{opt}$ can be determined using phase-only modulation as $$a_{opt} = \operatorname*{argmax}_{\underline{a}_1^+ \in P_c^M} \tau(\underline{a}_1^+) = \operatorname*{argmax}_{\underline{a}_1^+ \in P_c^M} \frac{\|S_{21} \cdot \underline{a}_1^+\|_2^2}{\|\underline{a}_1^+\|_2^2} = \operatorname*{argmax}_{\underline{a}_1^+ \in P_1^M} \|S_{21} \cdot \underline{a}_1^+\|_2^2. \quad \text{Equation 8}$$

The incident power constraint requires that $c=1$ and, therefore, $\underline{a}_1^+ \in P_1^M$ and $\underline{a}_{opt} \in P_1^M$. Where $c=1$, the additional phase vector form $\underline{p}(\underline{\theta}) := \underline{p}(\underline{\theta}; 1)$ may also be defined. The optimal wavefront may then be determined as a phase-only modulated wavefront $\underline{a}_{opt} = \underline{p}(\underline{\theta}_{opt})$, where the optimal phase vector $\underline{\theta}_{opt}$ may be determined as a phase vector $\underline{\theta}$ for which transmission coefficient achieves its maximum value for a highly scattering random medium 100 with scattering matrix S, as $$\begin{aligned} \underline{\theta}_{opt} &= \operatorname*{argmax}_{\underline{\theta}} (\underline{p}(\underline{\theta}))^H \cdot S_{21}^H \cdot S_{21} \cdot \underline{p}(\underline{\theta}) = \\ &\quad = (\underline{p}(\underline{\theta}))^H \cdot (I - S_{11}^H \cdot S_{11}) \underline{p}(\underline{\theta}) \\ &\operatorname*{argmin}_{\underline{\theta}} \|S_{11} \cdot \underline{p}(\underline{\theta})\|_2^2 = \operatorname*{argmin}_{\underline{\theta}} \Gamma(\underline{p}(\underline{\theta})). \end{aligned} \quad \text{Equation 9}$$

As above, the highly scattering random medium 100 can be approximated as a lossless medium, in which case the optimal phase vector $\underline{\theta}_{opt}$ may be obtained instead by minimizing the backscatter (represented by the reflection coefficient $\Gamma$) as $$a_{opt} = \operatorname*{argmin}_{\underline{a}_1^+ \in P_1^M} \|S_{11} \cdot \underline{a}_1^+\|_2^2, \quad \text{Equation 10}$$

In a lossless medium, using amplitude and phase modulation as discussed above is expected to yield an average optimal transmission efficiency as measured by the transmission coefficient $\tau$ of approximately 1. Due to the limitation on amplitude, phase-only modulation may not achieve perfect transmission, but phase-only modulation as described above is expected to yield an average optimal transmission efficiency as measured by the transmission coefficient $\tau$ of at least approximately $\pi/4$ in a lossless medium.

Iterative Algorithm for Maximizing Transmission Using Backscatter Analysis

The optimal wavefront $\underline{a}_{opt}$ or the optimal phase vector $\underline{\theta}_{opt}$ can be determined in a physically realizable iterative system using backscatter analysis, thereby eliminating the necessity of measuring the intensity of the transmitted wavefront that has passed through the highly scattering random medium 100 to the halfspace where $y > L$. In each iteration of the several algorithms below, the estimation of the optimal wavefront $\underline{a}_{opt}$ or the optimal phase vector $\underline{\theta}_{opt}$ is directly or indirectly updated until a numerically prespecified level of transmission is reached. Several embodiments of the system and method are discussed below.

One method of determining the optimal wavefront $\underline{a}_{opt}$ involves a steepest descent algorithm as set forth in Table 1 below. The steepest descent algorithm utilizes the negative gradient of the objective function $\|S_{11} \cdot \underline{a}_1^+\|_2^2$ from Equation 10 as a search direction to converge upon the optimal wavefront $\underline{a}_{opt}$ by iterative steps of predetermined step size $\mu > 0$. For any kth iteration of the steepest descent algorithm, the next iteration k+1 is determined by a step of size $\mu$ in the direction of the negative gradient of the objective function, expressed as $$\tilde{\underline{a}}_{1,(k)}^+ = \underline{a}_{1,(k)}^+ - \mu \frac{\partial \|S_{11} \cdot \underline{a}_1^+\|_2^2}{\partial \underline{a}_1^+}\bigg|_{\underline{a}_1^+ = \underline{a}_{1,(k)}^+}$$
$$= \underline{a}_{1,(k)}^+ - 2\mu S_{11}^H \cdot S_{11} \cdot \underline{a}_{1,(k)}^+,$$

Equation 11 where $\underline{a}_{1,(k)}^+$ represents the modal coefficient vector of the wavefront produced at the kth iteration of the algorithm. In each iteration, a refined wavefront with modal coefficient vector $\tilde{\underline{a}}_{1,(k)}^+$ is determined as indicated in line 6 of Table 1. The refined wavefront with modal coefficient vector $\tilde{\underline{a}}_{1,(k)}^+$ is further normalized as indicated in line 7 of Table 1 to obtain $\underline{a}_{1,(k+1)}^+$.

TABLE 1

1: Input: $\underline{a}_{1,(0)}^+$ = Initial random vector with unit norm
2: Input: $\mu > 0$ = step size
3: Input: $\epsilon$ = Termination condition
4: k = 0
5: while $\|S_{11} \cdot \underline{a}_{1,(k)}^+\|_2^2 > \epsilon$ do
6:   $\tilde{\underline{a}}_{1,(k)}^+ = \underline{a}_{1,(k)}^+ - 2\mu S_{11}^H \cdot S_{11} \cdot \underline{a}_{1,(k)}^+$
7:   $\underline{a}_{1,(k+1)}^+ = \tilde{\underline{a}}_{1,(k)}^+ / \|\tilde{\underline{a}}_{1,(k)}^+\|_2$
8:   k = k + 1
9: end while The first modal coefficient vector $\underline{a}_{1,(0)}^+$ at iteration k=0 may be the modal coefficient vector of any wavefront such that the modal coefficient vector has a unit norm. Alternatively, an additional wavefront may be selected and a first modal coefficient vector $\underline{a}_{1,(0)}^+$ be determined by normalizing the modal coefficient of the selected wavefront. The iteration repeats until the termination condition is reached, at which point the iterative refinement of the wavefront concludes. The final refined wavefront is taken as an approximation of the optimal wavefront $\underline{a}_{opt}$. The termination condition occurs when the backscatter intensity $\|S_{11} \cdot \underline{a}_{1,(k)}^+\|_2^2$ reaches or drops below a present level of $\in$.

To physically implement the steepest descent algorithm, the gradient of the objective function may be rewritten as $$S_{11}^H \cdot S_{11} \underline{a}_{1,(k)}^+ = F \cdot S_{11}^* \cdot F \cdot S_{11} \cdot \underline{a}_{1,(k)}^+ = F \cdot (S_{11} \cdot (F \cdot (S_{11} \cdot \underline{a}_{1,(k)}^+)^*))^*$$

Equation 12 where F is defined as the matrix resulting from applying the operation flipud(*) to the identity matrix I (i.e., F=flipud(I)). The operation flipud(*) takes as its argument a vector or a matrix and flips the argument vector or matrix upside down such that the first row becomes the last row, the second row becomes the penultimate row, and so on. The above Equation 12 is physically realizable using the double phase conjugation method described below.

Double phase conjugation consists of (1) time reversing a wavefront, (2) transmitting the time reversed wavefront into the highly scattering random medium 100, and (3) time reversing the resulting backscatter wavefront. Where the starting wavefront used in the double phase conjugation method is the backscatter wavefront produced by transmitting the wavefront with modal coefficient vector $\underline{a}_{1,(k)}^+$ into the highly scattering random medium 100, double phase conjugation produces the objective function gradient as indicated in Equation 12. This process depends upon three matrix-vector operations: $S_{11} \cdot \underline{a}_1^+$, $F \cdot (\underline{a}_1^-)^*$, and $S_{11}^H \cdot \underline{a}_1^-$. Each of these matrix-vector operations may be performed mathematically or physically. In some embodiments, the example system 200 in FIG. 2 may be used to perform these operations.

Figure 2:
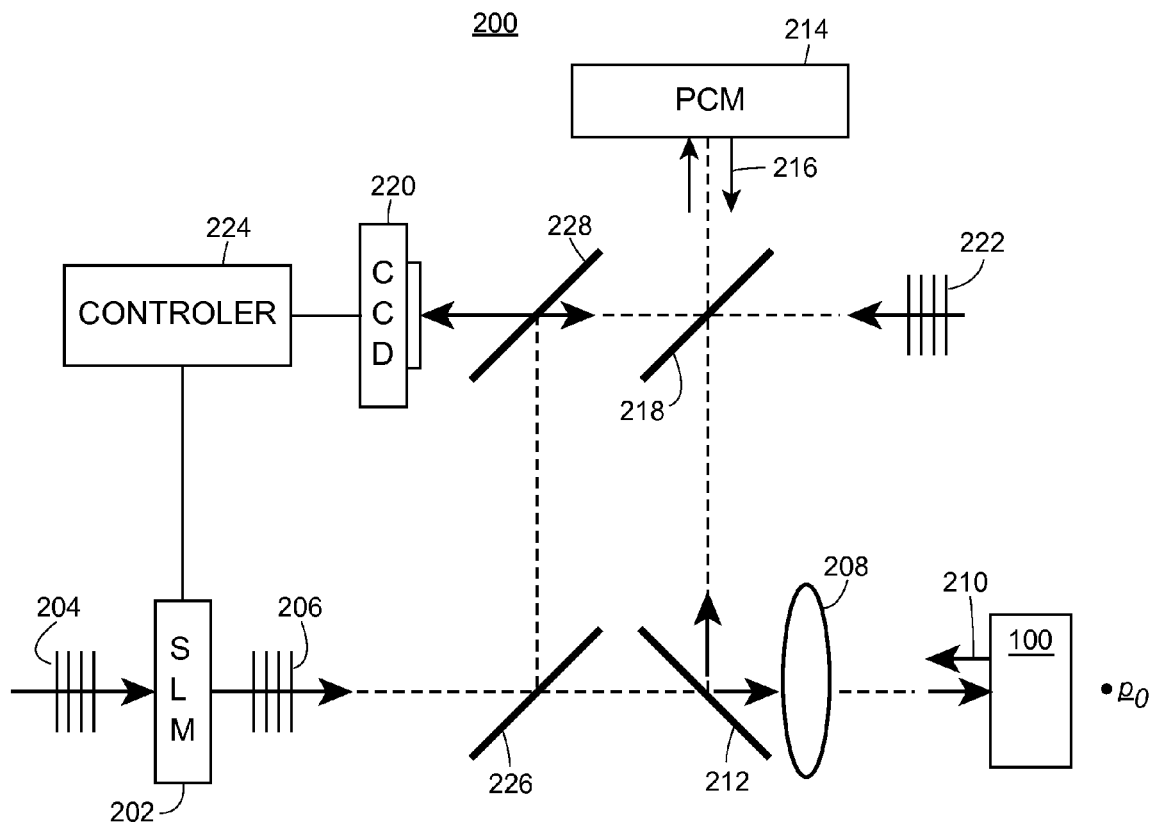
FIG. 2 illustrates an example system for increasing transmission through a highly scattering random medium.

FIG. 2 illustrates an example system for increasing transmission through the highly scattering random medium 100. The example system 200 may be used to iteratively refine a wavefront for transmission into the highly scattering random medium 100. In an embodiment of the system 200, a spatial light modulator (SLM) 202 is used to modulate an input wave 204 to produce a wavefront 206. Alternatively, a wavefront 206 may be produced directly or indirectly by any transmitter or modulator, using any technique known in the art. The wavefront 206 may then be focused on the highly scattering random medium 100 by passing through a lens 208. In some embodiments, the resulting backscatter wavefront 210 may pass back through the lens 208 and be redirected using a beam splitter 212. The backscatter wavefront 210 may then be time reversed as discussed below using a phase-conjugate mirror (PCM) 214. In some embodiments, the resulting time-reversed backscatter wavefront 216 may then be redirected using beam splitter 212, focused using lens 208, and transmitted into the highly scattering random medium 100 to produce another backscatter wavefront 210, which may pass back through the lens 208, be redirected using a beam splitter 212, and be time reversed using PCM 214 to produce another time-reversed backscatter wavefront 216. In some embodiments, the wavefront 216 may be redirected using a beam splitter 218 to reach a detector 220. The detector 220 may be a charge-coupled device or any other analog or digital transducer capable of detecting the wavefront 216. In some embodiments, the detector 220 may also receive a holographic reference wave 222. The holographic reference wave 222 may be used to determine the modal coefficient vector of the wavefront 216 using known digital holography techniques. Information corresponding to the wavefronts 216 and 222 detected at the detector 220 may be transmitted to a controller 224. The transmitted information may include the raw or processed measurements at the detector 220, or it may include one or more modal coefficient vectors or other identifying information associated with the wavefronts. In some embodiments, the controller 224 may be configured to reconstruct the wavefront 216 from the information received from the detector 220. In some embodiments, the controller 224 may perform computational matrix or vector operations to the modal coefficient vector of wavefront 216 to determine a new wavefront. The controller may then control the SLM 202 or other wave source to produce another wavefront 206 for transmission into the highly scattering random medium 100. Thus, the system 200 may be used to refine a wavefront by an iterative process to increase transmission through the highly scattering random medium 100. In some embodiments, the system 200 may also be used to focus a wavefront using an iterative process to increase field intensity at a point $\underline{p}$.

Operation $S_{11} \underline{a}_1^+$ may be physically implemented by transmitting a wavefront 206 with modal coefficient vector $\underline{a}_1^+$ into the highly scattering random medium 100 and measuring (not shown) the resulting backscatter wavefront 210 with coefficient vector $\underline{a}_1^-$. The modal coefficient vector $\underline{a}_1^-$ may be determined from backscatter intensity measurements using known digital holography techniques implemented on the controller 224. In some embodiments, the modal coefficient vector $\underline{a}_1^-$ may not be determined; the wavefront 210 with modal coefficient vector $\underline{a}_1^-$ may instead be utilized without determining the vector $\underline{a}_1^-$, as below.

Operation $F \cdot (\underline{a}_1^-)^*$ may be physically implemented by time reversing the wavefront 210 with coefficient vector $\underline{a}_1^-$. In some embodiments, the wavefront 210 may be time reversed by phase conjugation mirroring using PCM 214. Alternatively, the wavefront may be time reversed by determining the coefficient vector $\underline{a}_1^-$ and constructing a time reversed wavefront using the controller 224 by calculating the product of F and the complex conjugate of $\underline{a}_1^-$.

Operation $S_{11}^H \cdot \underline{a}_1^-$ may be physically implemented by the double phase conjugation method by time reversing the wavefront 210 with modal coefficient $\underline{a}_1^-$, transmitting the time-reversed wavefront 216 into the highly scattering random medium 100, and time reversing the resulting backscatter wavefront 210. Where the highly scattering random medium 100 exhibits reciprocity, the reflection matrix $S_{11}$ must be such that the following relationship holds: $S_{11}^H = F \cdot S_{11}^* \cdot F$. As a result, if transmitting $\underline{a}$ wave $\underline{a}$ into a highly scattering random medium 100 with reflection matrix $S_{11}$ produces a backscatter wave $\underline{b}$, then transmitting a wave $F \cdot (\underline{a})^*$ into a highly scattering random medium 100 with reflection matrix $S_{11}^H$ produces a backscatter wave $F \cdot (\underline{b})^*$. From this relationship, the operation $S_{11}^H \cdot \underline{a}_1^-$ may be expressed as $F \cdot S_{11}^*$, $F \cdot \underline{a}_1^- = F \cdot (S_{11} \cdot (F \cdot (\underline{a}_1^-)^*))^*$. The operation $F \cdot (\underline{a}_1^-)^*$ corresponds to a time reversal of the wavefront 210 with modal coefficient vector $\underline{a}_1^-$, so the double phase conjugation method applied to wavefront 210 with modal coefficient vector $\underline{a}_1^-$ obtained by transmitting wavefront 206 into the highly scattering random medium 100 corresponds to the matrix-vector operation $S_{11}^H \cdot \underline{a}_1^-$, each step of which may be implemented as described above.

Table 2 illustrates the steps of the kth iteration of the steepest descent method as physically implemented by applying the double phase conjugation method and the operations described above. In line 1, a first transmission wavefront 206 with modal coefficient vector $\underline{a}_{1,(k)}^+$ is transmitted into the highly scattering random medium 100, and the first backscatter wavefront 210 with modal coefficient vector $\underline{a}_1^-$ is obtained. Lines 2-4 correspond to the double phase conjugation method applied to the first backscatter wavefront 210 with modal coefficient vector $\underline{a}_1^-$. In line 2, the first backscatter wavefront 210 with modal coefficient vector $\underline{a}_1^-$ may be time reversed using PCM 214 to obtain the second transmission wavefront 216 with modal coefficient vector 4. In line 3, the second transmission wavefront 216 with modal coefficient vector $\underline{a}_1^+$ is transmitted into the highly scattering random medium 100, and a second backscatter wavefront 210 with modal coefficient vector $\underline{a}_1^-$ is obtained, which will not generally be the same as the first backscatter wavefront 210 with modal coefficient vector $\underline{a}_1^-$ obtained in line 1. In line 4, the second backscatter wavefront 210 with modal coefficient vector $\underline{a}_1^-$ may be time reversed using PCM 214 to obtain the updating wavefront 216 with modal coefficient vector 4, completing the double phase conjugation. In line 5, the wavefront $\underline{a}_{1,(k)}^+$ is refined in proportion to the step size µ and the modal coefficient vector $\underline{a}_1^+$ of updating wavefront 216 resulting from the double phase conjugation method to obtain a wave with modal coefficient vector $\tilde{\underline{a}}_1^+$. The modal coefficient vector $\underline{a}_1^+$ may be determined using known digital holography techniques implemented on the detector 220, the holographic reference wave 222, and the controller 224. Finally, in line 6, the refined wavefront $\tilde{\underline{a}}_1^+$ is normalized to obtain $\underline{a}_{1,(k+1)}^+$. The refinement and normalization in lines 5 and 6 may be performed using the controller 224. The iterative process in Table 2 terminates when the backscatter intensity of the first backscatter wavefront $\underline{a}_1^-$ falls below the present level of $\in$, as indicated by $\|\underline{a}_1^-\|_2^2 < \in$, which may also be determined using the controller 224.

TABLE 2

| Vector Operation | Physical Operation |
|---|---|
| 1: $\underline{a}_1^- = S_{11} \cdot \underline{a}_{1,(k)}^+$ | 1: $\alpha_{1,(k)}^+ \xrightarrow{\text{Backscatter}} \alpha_1^-$ |
| 2: $\underline{a}_1^+ = F \cdot (\underline{a}_1^-)^*$ | 2: $\alpha_1^- \xrightarrow{\text{PCM}} \alpha_1^+$ |
| 3: $\underline{a}_1^- = S_{12} \cdot \underline{a}_1^+$ | 3: $\alpha_1^+ \xrightarrow{\text{Backscatter}} \alpha_1^-$ |
| 4: $\underline{a}_1^+ = F \cdot (\underline{a}_1^-)^*$ | 4: $\alpha_1^- \xrightarrow{\text{PCM}} \alpha_1^+$ |
| 5: $\underline{a}_1^+ = \underline{a}_{1,(k)}^+ - 2\mu\underline{a}_1^+$ | 5: $\underline{a}_1^+ = \underline{a}_{1,(k)}^+ - 2\mu\underline{a}_1^+$ |
| 6: $\underline{a}_{1,(k+1)}^+ = \underline{a}_1^+ / \|\underline{a}_1^+\|_2$ | 6: $\tilde{\alpha}_1^+ \xrightarrow{\text{Normalization}} \alpha_{1,(k+1)}^+$ |

The steepest descent method may also be implemented in embodiments comprising phase-only modulation of the wavefronts. As discussed above, phase-only modulation requires that all transmitted wavefronts have incident power $\|\underline{a}_1^+\|_2 = 1$, or $\underline{a}_1^+ \in P_1^M$. Table 3 illustrates the steepest descent method adjusted for phase-only modulation. In addition to the steps described above, the first backscatter wavefront 210 with modal coefficient vector $\underline{a}_1^-$ is used to determine a scalar $\bar{a}$ of the average magnitude of the modal coefficients of the first backscatter wavefront 210 with modal coefficient vector $\underline{a}_1^-$ as follows:

$$\bar{a} = \frac{\sum_{n=-N}^{N} |a_{1,n}^-|}{\sqrt{M}} \qquad \text{Equation 13}$$

TABLE 3

| Vector Operation | Physical Operation |
|---|---|
| 1: $\underline{a}_1^- = S_{11} \cdot \underline{a}_{1,(k)}^+$ | 1: $\alpha_{1,(k)}^+ \xrightarrow{\text{Backscatter}} \alpha_1^-$ |
| 2: $\bar{\alpha} = \frac{\sum_{n=-N}^{N} |\alpha_{1,n}^-|}{\sqrt{M}}$ | 2: $\bar{\alpha} = \frac{\sum_{n=-N}^{N} |\alpha_{1,n}^-|}{\sqrt{M}}$ |
| 3: $\underline{a}_1^- \leftarrow p(/\alpha_1^-)$ | 3: $\underline{a}_1^- \leftarrow p(/\alpha_1^-)$ |
| 4: $\underline{a}_1^+ = F \cdot (\underline{a}_1^-)^*$ | 4: $\alpha_1^- \xrightarrow{\text{PCM}} \alpha_1^+$ |
| 5: $\underline{a}_1^- = S_{11} \cdot \underline{a}_1^+$ | 5: $\alpha_1^+ \xrightarrow{\text{Backsetter}} \alpha_1^-$ |
| 6: $\underline{a}_1^+ = F \cdot (\underline{a}_1^-)^*$ | 6: $\alpha_1^- \xrightarrow{\text{PCM}} \alpha_1^+$ |
| 7: $\underline{a}_1^+ = \underline{a}_{1,(k)}^+ - 2\mu\bar{\alpha}\underline{a}_1^+$ | 7: $\underline{a}_1^+ = \underline{a}_{1,(k)}^+ - 2\mu\bar{\alpha}\underline{a}_1^+$ |
| 8: $\underline{a}_{1,(k+1)}^+ = p(/\tilde{\alpha}_1^+)$ | 8: $\underline{a}_{1,(k+1)}^+ = p(/\tilde{\alpha}_1^+)$ |

This may be implemented by detecting the first backscatter wavefront 216 with detector 220, then computing the average magnitude scalar $\bar{a}$ using the controller 224. Using this physically measurable scalar, the gradient of the objective function $S_{11}^H \cdot S_{11} \cdot \underline{a}_{1,(k)}^+$ is physically implementable in a method or system utilizing phase-only modulation as $\bar{a} S_{11}^H \cdot \underline{p}(\angle(S_{11} \cdot \underline{a}_{1,(k)}^+))$. Once the average magnitude scalar $\bar{a}$ has been determined in line 2, the phase-only modal coefficient vector of the first backscatter wavefront with modal coefficient vector $\underline{p}(\angle \underline{a}_1^-)$ is determined in line 3. This may be implemented by the controller 224, which may control the SLM 202 to produce the phase-only first backscatter wavefront 206 with modal coefficient vector $\underline{p}(\angle \underline{a}_1^-)$. The double phase conjugation method is then applied to the phase-only first backscatter wavefront 206 with modal coefficient vector $\underline{p}(\angle \underline{a}_1^-)$ using beam splitters 226 and 228 to direct the wave 206 to the PCM 214. The updating wavefront 216 with modal coefficient vector $\underline{a}_1^+$ may be obtained by implementing the double phase conjugation method as above starting with the phase-only first backscatter wavefront 206. The coefficient vector $\underline{a}_1^+$ of updating wavefront 216 may be determined using the detector 220 and controller 224, as above. In line 7, the controller 224 refines the wavefront $\underline{a}_{1,(k)}^+$ in proportion to the step size $\mu$, the average magnitude scalar $\bar{a}$, and the updating wavefront modal coefficient vector $\underline{a}_1^+$ to obtain a modal coefficient vector $\underline{\tilde{a}}_1^+$. To satisfy the incident power constraint, the controller 224 uses only the phase of $\underline{\tilde{a}}_1^+$ to produce the wavefront $\underline{a}_{1,(k+1)}^+ = \underline{p}(\angle \underline{\tilde{a}}_1^+) \in P_1^M$ using the SLM 202 in line 8. The iterative process in Table 3 terminates when the backscatter intensity of the first backscatter wavefront $\underline{a}_1^-$ falls below the present level of $\in$, as above.

The steepest descent method using phase-only modulation described above first determines an iteratively refined approximation $\underline{\tilde{a}}_1^+$ of the optimal wavefront $\underline{a}_{opt}$ and then projects it onto the set of phase-only modulated wavefronts $\underline{a}_{1,(k+1)}^+ = \underline{p}(\angle \underline{\tilde{a}}_1^+) \in P_1^M$. Table 4 illustrates the phase-only gradient method, which updates only the phase of the incident wavefront $\underline{\theta}_{1,(k)}^+$ to iteratively approximate the optimal phase vector $\underline{\theta}_{opt}$. In this method, the objective function of interest is the intensity of the backscatter of a phase-only modulated wavefront $\|S_{11} \cdot \underline{p}(\theta)\|_2^2$, the negative gradient of which is used to refine the phase of the incident wavefront $\underline{\theta}_{1,(k)}^+$ in each iteration as follows:

$$\underline{\theta}_{1,(k+1)}^+ = \underline{\theta}_{1,(k)}^+ - \sqrt{M} \mu \frac{\partial \|S_{11} \cdot \underline{p}(\theta)\|_2^2}{\partial \theta}\bigg|_{\theta = \underline{\theta}_{1,(k)}^+}, \quad \text{Equation 14}$$

This equation may be rewritten as follows:

$$\underline{\theta}_{1,(k+1)}^+ = \underline{\theta}_{1,(k)}^+ - 2\sqrt{M} \mu Im[\text{diag}\{\tilde{p}(-\underline{\theta}_{1,(k)}^+)\} \cdot S_{11}^H \cdot S_{11} \cdot \underline{p}(\underline{\theta}_{1,(k)}^+)]. \quad \text{Equation 15}$$

where Im(•) denotes the operator that returns the imaginary part of the argument and $\text{diag}\{\underline{p}(-\underline{\theta}_{1,(k)}^+)\}$ denotes a diagonal matrix with entries $\underline{p}(\underline{\theta}_{1,(k)}^+)$ along its diagonal. As above, the incident power constrain prevents the physical implementation of $S_{11}^H \cdot S_{11} \cdot \underline{p}(\underline{\theta}_{1,(k)}^+)$, so $\bar{a} S_{11}^H \cdot \underline{p}(\angle(S_{11} \cdot \underline{p}(\underline{\theta}_{1,(k)}^+)))$ is substituted where $\bar{a}$ is the average magnitude scalar defined above. Therefore, iterative refinement of the wavefront according to Equation 15 above can be rewritten in a physically implementable form as $$\underline{\theta}_{1,(k+1)}^+ = \underline{\theta}_{1,(k)}^+ - 2\sqrt{M} \mu \bar{a} IM[\text{diag}\{\underline{p}(-\underline{\theta}_{1,(k)}^+)\} \cdot S_{11}^H \cdot \underline{p}(\angle S_{11} \cdot \underline{p}(\underline{\theta}_{1,(k)}^+))], \quad \text{Equation 16}$$

TABLE 4

| Vector Operation | Physical Operation |
|---|---|
| 1: $\underline{a}_1^- = S_{11} \cdot \underline{p}(\underline{\theta}_{1,(k)}^+)$ | 1: $\underline{p}(\underline{\theta}_{1,(k)}^+) \xrightarrow{\text{Backscatter}} \underline{\alpha}_1^-$ |
| 2: $\bar{\alpha} = \frac{\sum_{n=-N}^{N} |\alpha_{1,n}|}{\sqrt{M}}$ | 2: $\bar{\alpha} = \frac{\sum_{n=-N}^{N} |\alpha_{1,n}^-|}{\sqrt{M}}$ |
| 3: $\underline{a}_1^- \leftarrow \underline{p}(\angle \underline{a}_1^-)$ | 3: $\underline{\alpha}_1^- \leftarrow \underline{p}(\angle \underline{\alpha}_1^-)$ |
| 4: $\underline{a}_1^+ = F \cdot (\underline{a}_1^-)^*$ | 4: $\underline{\alpha}_1^- \xrightarrow{\text{PCM}} \underline{\alpha}_1^+$ |
| 5: $\underline{a}_1^- = S_{11} \cdot \underline{a}_1^+$ | 5: $\underline{\alpha}_1^+ \xrightarrow{\text{Backscatter}} \underline{\alpha}_1^-$ |
| 6: $\underline{a}_1^+ = F \cdot (\underline{a}_1^-)^*$ | 6: $\underline{\alpha}_1^- \xrightarrow{\text{PCM}} \underline{\alpha}_1^+$ |
| 7: $\underline{\theta}_{1,(k+1)}^+ = \underline{\theta}_{1,(k)}^+ - 2\sqrt{M} \mu \bar{\alpha} 1m[\text{diag}\{\underline{p}(-\underline{\theta}_{1,(k)}^+)\} \cdot \underline{\alpha}_1^+]$ | |

In line 1 of Table 4, a first transmission wavefront 206 with phase vector $\underline{p}(\underline{\theta}_{1,(k)}^+)$ is transmitted into the highly scattering random medium 100, and the first backscatter wavefront 210 with modal coefficient vector $\underline{a}_1^-$ is obtained. Lines 2-6 determine the average magnitude scalar $\bar{a}$ and implement the double phase conjugation method as above. In line 7, the controller 224 refines the phase of the incident wavefront $\underline{\theta}_{1,(k)}^+$ according to Equation 16, using the average magnitude scalar $\bar{a}$ and the results of the double phase conjugation process. The refined phase vector $\underline{\theta}_{1,(k+1)}^+$ may be directly computed using the controller 224. The iterative process in Table 4 terminates when the backscatter intensity of the first backscatter wavefront $\underline{a}_1^-$ falls below the present level of $\in$, as above.

The methods described above amplify the highly backscattering component of the wavefront 206 with modal coefficient vector $\underline{a}_{1,(k)}^+$ or $\underline{p}(\underline{\theta}_{1,(k)}^+)$ in a manner analogous to time-reversal focusing, allowing the highly backscattering component to be iteratively removed from the wavefront. The refined wavefront will then produce less backscatter, which makes measurement of the backscatter modal coefficient vector increasingly difficult in subsequent iterations of the method. Furthermore, the step size $\mu$ must be set to a value that ensures convergence of the method. The conjugate gradient method described below maintains a high backscatter field intensity and does not require the selection of a step size.

Another method of determining the optimal wavefront $\underline{a}_{opt}$ involves a conjugate gradient algorithm as set forth in Table 5. The conjugate gradient method involves iteratively determining the backscatter minimizing wavefront $$\underline{a}_{1,(k+1)}^+ = \underline{a}_{1,(k)}^+ + \mu_{(k+1)} \underline{d}_{(k)}, \quad \text{Equation 17}$$

where $\mu_{(k+1)}$ is a step size and $d_{(k)}$ is a search direction. Specifically, the step size is determined as $$\mu_{(k+1)} = \|\underline{r}_{(k+1)}\|_2^2 / \|S_{11} \cdot \underline{d}_{(k)}\|_2^2 \quad \text{Equation 18}$$

and the search direction is determined as $$\underline{d}_{(k+1)} = \underline{r}_{(k+1)} + \beta_{(k+1)} \underline{d}_{(k)} \quad \text{Equation 19}$$

where $$\beta_{(k+1)} = \|\underline{r}_{(k+1)}\|_2^2 / \|\underline{r}_{(k)}\|_2^2 \quad \text{Equation 20}$$

and the residual vector $r_{(k+1)}$ is determined as the physically realizable product $$\underline{r}_{(k+1)} = -S_{11}^H \cdot S_{11} \cdot \underline{a}_{1,(k+1)}^+. \quad \text{Equation 21}$$

Analogous to the steepest descent method above, the conjugate gradient method uses a termination condition such that iterative refinement terminates when $\|k_{(k+1)}\|_2 \leq \epsilon$, which may be implemented at controller 224. The initial modal coefficient vector as $\underline{a}_{a,(0)}^+$ may be any unit vector, and $\underline{d}_{(0)}$ and $\hat{r}_{(0)}$ may both be set to $-S_{11}^H \cdot S_{11} \cdot \underline{a}_{1,(0)}^+$ by application of the double phase conjugation method applied to the backscatter wavefront $\underline{a}_1^-$ obtained by transmitting $-\underline{a}_{1,(0)}^+$ into the highly scattering random medium 100.

Table 5 illustrates the vector and physical operations of each iteration of the conjugate gradient method. It should be noted that modal coefficient vector $\underline{a}_{1,(k)}^+$ is refined in each iteration at the controller 224, but the wavefront with modal coefficient vector $\underline{a}_{1,(k)}^+$ is not transmitted into the highly scattering random medium 100 until the termination condition has been met. This has the advantage of maintaining a higher backscatter field intensity throughout the iterative process, thereby reducing the role of noise and measurement error in the system. In line 1, a first transmission wavefront 206 with modal coefficient vector $\underline{d}_{(k)}$ is generated and transmitted into the highly scattering random medium 100, and the first backscatter wavefront 210 with modal coefficient vector $\underline{d}_1^-$ is obtained. Lines 2-4 correspond to the double phase conjugation method applied to the first backscatter wavefront $\underline{d}_1^-$. In line 2, the first backscatter wavefront 210 with modal coefficient vector $\underline{d}_1^-$ is time reversed using PCM 214 or another method to obtain the second transmission wavefront 216 with modal coefficient vector $\underline{d}_1^+$. In line 3, the second transmission wavefront 216 with modal coefficient vector $\underline{d}_1^+$ is transmitted into the highly scattering random medium 100, and a second backscatter wavefront 210 with modal coefficient vector $\underline{d}_i^-$ is obtained, which will not generally be the same as the first backscatter wavefront 210 with modal coefficient vector $\underline{d}_1^-$ obtained in line 1. In line 4, the second backscatter wavefront 210 with modal coefficient vector $\underline{d}_1^-$ is time reversed using PCM 214 or another method to obtain the updating wavefront 216 with modal coefficient vector $\underline{d}$, completing the double phase conjugation. The modal coefficient vector $\hat{d}$ of the updating wavefront 216 may be determined using the detector 220, holographic reference wave 222, and controller 224 using known digital holography techniques. In lines 5-8, the updated step size $\mu_{(k+1)}$, residual vector $r_{(k+1)}$, factor $\beta_{(k+1)}$, and search direction $d_{(k+1)}$ are determined using the modal coefficient vector $\underline{d}$. These updates may be directly or indirectly computed by standard matrix or vector operations using the controller 224. Finally, line 9 indicates the iterative refinement of the wavefront $\underline{a}_{1,(k)}^+$ using the updated step size $\mu_{(k+1)}$ and the search direction $d_{(k)}$, and line 10 indicates the normalization of the refined wavefront $\underline{a}_{1,(k+1)}^+$. Both steps 9 and 10 may be implemented using controller 224. When the termination condition is achieved, iterative refinement terminates, and the refined wavefront 206 with modal coefficient vector $\underline{a}_{1,(k+1)}^+$ is transmitted into the highly scattering random medium 100.

TABLE 5

| Vector Operation | Physical Operation |
|---|---|
| 1: $\underline{d}_1^- = S_{11} \cdot \underline{d}_{(k)}$ | 1: $\underline{d}_{(k)} \xrightarrow{Backscatter} \underline{d}_1^-$ |
| 2: $\underline{d}_1^+ = F \cdot (\underline{d}_1^-)^*$ | 2: $\underline{d}_1^- \xrightarrow{PCM} \underline{d}_1^+$ |
| 3: $\underline{d}_1^- = S_{11} \cdot \underline{d}_1^+$ | 3: $\underline{d}_1^+ \xrightarrow{Backscatter} \underline{d}_1^-$ |

TABLE 5-continued

| Vector Operation | Physical Operation |
|---|---|
| 4: $\underline{d} = F \cdot (\underline{d}_1^-)^*$ | 4: $\underline{d}_1^- \xrightarrow{PCM} \underline{d}$ |
| 5: $\mu_{(k+1)} = \|\underline{r}_{(k)}\|_2^2 / (\underline{d}_{(k)}^H \cdot \underline{d})$ | 5: $\mu_{(k+1)} = \|\underline{r}_{(k)}\|_2^2 / (\underline{d}_{(k)}^H \cdot \underline{d})$ |
| 6: $\underline{r}_{(k+1)} = \underline{r}_{(k)} - \mu_{(k+1)} \underline{d}$ | 6: $\underline{r}_{(k+1)} = \underline{r}_{(k)} - \mu_{(k+1)} \underline{d}$ |
| 7: $\beta_{(k+1)} = \|\underline{r}_{(k+1)}\|_2^2 / \|\underline{r}_{(k)}\|_2^2$ | 7: $\beta_{(k+1)} = \|\underline{r}_{(k+1)}\|_2^2 / \|\underline{r}_{(k)}\|_2^2$ |
| 8: $\underline{d}_{(k+1)} = \underline{r}_{(k+1)} + \beta_{(k+1)} \underline{d}_{(k)}$ | 8: $\underline{d}_{(k+1)} = \underline{r}_{(k+1)} + \beta_{(k+1)} \underline{d}_{(k)}$ |
| 9: $\underline{a}_{1,(k+1)}^+ = \underline{a}_{1,(k)}^+ + \mu_{(k+1)} \underline{d}_{(k)}$ | 9: $\underline{a}_{1,(k+1)}^+ = \underline{a}_{1,(k)}^+ + \mu_{(k+1)} \underline{d}_{(k)}$ |
| 10: $\underline{a}_{1,(k+1)}^+ = \underline{a}_{1,(k+1)}^+ / \|\underline{a}_{1,(k+1)}^+\|_2$ | 10: $\underline{a}_{1,(k+1)}^+ = \underline{a}_{1,(k+1)}^+ / \|\underline{a}_{1,(k+1)}^+\|_2$ |

Focusing Transmission Through Highly Scattering Random Media

The methods discussed above may also be applied to focus transmission through the highly scattering random medium 100 to a location $\rho_0$ in the halfspace where $y > L$. Since $\underline{a}_2^- = 0$, the transmitted wave is $\underline{a}_2^+ = S_{21} \cdot \underline{a}_1^+$. Combining this with Equation 1, the field at location $\rho_0$ is $$e_2^+(\rho_0) = \underbrace{[h_{-N} e^{-jk_N^+ \cdot \rho_0} \ldots h_{-N} e^{-jk_N^+ \cdot \rho_0}]}_{=: \underline{f}(\rho_0)''} \cdot S_{21} \cdot \underline{a}_1^+. \quad \text{Equation 22}$$

so the optimal focusing wavefront with modal coefficient vector $\underline{a}_{foc}$ may be determined as the power-constrained wavefront that maximizes the intensity of the field at location $\rho_0$ by transmission through the highly scattering random medium 100 with transmission matrix $S_{21}$ as follows:

$$\underline{a}_{foc} = \underset{\underline{a}_1^+}{\operatorname{argmax}} \frac{\|e_2^+(\rho_0)\|_2^2}{\|\underline{a}_1^+\|_2^2} = \underset{\|\underline{a}_1^+\|_2 = 1}{\operatorname{argmax}} \left\| \underbrace{\underline{f}^H(\rho_0) \cdot S_{21}}_{=: \underline{c}(\rho_0)''} \cdot \underline{a}_1^+ \right\|_2^2, \quad \text{Equation 23}$$

the solution to which is $$\underline{a}_{foc} = \frac{\underline{c}(\rho_0)}{\|\underline{c}(\rho_0)\|_2} = \frac{S_{21}^H \cdot \underline{f}(\rho_0)}{\|S_{21}^H \cdot \underline{f}(\rho_0)\|_2}. \quad \text{Equation 24}$$

The optimal focusing wavefront may be determined by time reversing the wavefront received by placing a wave source at location $\rho_0$. This has motivated work that determines the optimal focusing wavefront using O(M) measurements of the intensity at location $\rho_0$. The method described herein, however, uses the K eigen-wavefronts with transmission coefficients near unity (i.e., $\tau \approx 1$) to determine the optimal focusing wavefront with modal coefficient vector $\underline{a}_{foc}$ using on the order of K measurements of the intensity at location $\rho_0$.

Expressing the optimal focusing wavefront in terms of the singular value decomposition of transmission matrix $S_{21}$ in Equation 24 above yields the expression $$\underline{a}_{foc} \propto S_{21}^H \cdot \underline{f}(\rho_0) = \sum_{i=1}^M \sigma_i \underbrace{(\underline{u}_i^H \cdot \underline{f}(\rho_0))}_{=: w_i} \underline{v}_i = \sum_{i=1}^M \sigma_i w_i \underline{v}_i. \quad \text{Equation 25}$$

where $\sigma_i$ is the singular value associated with the left and right singular vectors $\underline{u}_i$ and $\underline{v}_i$, respectively. By convention, the singular values are arranged in descending orders so that $\sigma_1 \geq \sigma_2 \geq \ldots \geq \sigma_M$. The transmission coefficient for each right singular vector is $\tau(\underline{v}_i) = \sigma_i^2$, so only the K eigen-wavefronts with high transmission will significantly contribute to the field at location $\rho_0$. The remaining right singular vectors will have transmission coefficients close to zero. Since there are typically K>>M highly transmitting eigen-wavefronts, determining the optimal focusing wavefront with modal coefficient vector $\underline{a}_{foc}$ as a superposition of these K eigen-wavefronts of transmission matrix $S_{21}$ will produce an approximation of the optimal focusing wavefront using fewer measurements—O(K)>>O(M). As before, these K high-transmission eigen-wavefronts of transmission matrix $S_{21}$ correspond precisely to the K low-reflection eigen-wavefronts of reflection matrix $S_{11}$ in a lossless setting. Therefore, the optimal focusing wavefront with modal coefficient vector $\underline{a}_{foc}$ may be approximated using O(K) backscatter measurements to determine the backscattering-minimizing eigen-wavefronts of reflection matrix $S_{11}$ and O(K) intensity measurements at location $\rho_0$.

To determine the optimal focusing wavefront in an iterative manner, a generalized coordinate descent method for amplitude and phase optimization is used. This involves an $M \times N_B$ matrix $B = [\underline{b}_1 \ldots \underline{b}_{N_B}]$ with orthonormal columns, such that $B^H \cdot B = I_{N_B}$. Thus, $N_B$ denotes the number of orthonormal basis vectors. The modal coefficient vector $\underline{a}_1^+$ in Equation 24 can then be expanded in terms of the basis vectors given by the columns of B as $$\underline{a}_1^+ = \sum_{i=1}^{N_B} p_i e^{j\phi_i} \underline{b}_i, \quad \text{Equation 26}$$

where $p_i \geq 0$ and $\phi_i \in [-\pi, \pi]$ are the unknown amplitudes and phases, respectively. The amplitudes $p_l$ may be approximated by transmitting a wavefront 206 with modal coefficient vector $\underline{a}_1^+ = \underline{b}_l$ into the highly scattering random medium 100 for each $l=1, \ldots, N_B$, measuring the intensity of the field $I_l$ at the location $\rho_0$ using a charge-coupled device or other detector (not shown), and setting $p_l = \sqrt{I_l}$ using the controller 224. The phases $\phi_l$ may similarly be approximated by setting each phase $\phi_l$ to any starting value, then sequentially finding the phase that optimizes the intensity of the field $I_l$ at the location $\rho_0$ for each $l=1, \ldots, N_B$. This may be accomplished using a simple line search to scan the intensity measured at location $\rho_0$ over a fixed set of discretized values of the phase $\phi_l$, which may be implemented by the controller 224 controlling the SLM 202. Alternatively, other known or later developed algorithms to approximate each phase $\phi_l$. Both of the processes of determining the amplitudes $p_l$ and the phases $\phi_l$ may be accomplished using $O(N_B)$ measurements. The number of measurements can be reduced to O(K) by using the K right singular eigenvectors $\underline{v}_i$ of reflection matrix $S_{11}$ that minimize backscattering as the $N_B$ columns of matrix B.

The K right singular eigenvectors $\underline{v}_i$ of reflection matrix $S_{11}$ that minimize backscattering correspond to the right singular eigenvectors $\underline{v}_i$ associated with the K smallest singular values $\sigma_i$ of reflection matrix $S_{11}$. The K smallest singular values $\sigma_i$ and right singular vectors $\underline{v}_i$ may be determined using the Lanczos algorithm. The Lanczos algorithm iteratively produces a tridiagonal matrix H, the eigenvalues and eigenvectors of which approximate the eigenvalues and eigenvectors of $S_{11}^H \cdot S_{11}$. Table 6 illustrates an iteration of a physically implementable method corresponding to the Lanczos Algorithm that utilizes double phase conjugation, as described above. In the first iteration where k=1, the modal coefficient vector of the iterative wavefront $\underline{q}_{(k)}$ may be set to any unit norm vector and the coefficient $s_{(0)}=0$. In line 1, the iterate wavefront 206 with modal coefficient vector $\underline{q}_{(k)}$ is transmitted into the highly scattering random medium 100, and the backscatter wavefront 210 with modal coefficient vector $\underline{q}_1^-$ is obtained. Lines 2-4 correspond to the double phase conjugation method applied to the first backscatter wavefront 210 with modal coefficient vector $\underline{q}_1^-$ to obtain the wavefront 216 with modal coefficient vector $\underline{v}$, which may be determined using controller 224 from measurements at detector 220. In line 5, the kth diagonal entry $H_{k,k}$ in tridiagonal matrix H is determined as the product of the complex conjugate transpose of the modal coefficient vector $\underline{q}_{(k)}$ of the iterate wavefront 206 and modal coefficient vector $\underline{v}$. Line 6 updates the modal coefficient vector $\underline{v}$ using the product of the diagonal entry $H_{k,k}$ and the modal coefficient vector $\hat{\underline{q}}_{(k)}$ of the iterate wavefront 206 and the product of the previous iteration coefficient $s_{(k-1)}$ and the modal coefficient vector $\underline{q}_{(k-1)}$ of the previous iterative wavefront 206. In line 7, the entries in the diagonals of matrix H above and below the main diagonal are determined as the norm of modal coefficient vector $\underline{v}$, as is coefficient $s_{(k)}$. Finally, in line 8, the modal coefficient vector $\underline{q}_{(k+1)}$ of the next iterative wavefront 206 is determined as the quotient of updated modal coefficient vector $\underline{v}$ and coefficient $s_{(k)}$. The matrix and vector operations in lines 5-8 may be directly or indirectly computed using the standard matrix or vector operations implemented using the controller 224.

TABLE 6

| Vector Operation | Physical Operation |
| --- | --- |
| 1: $\underline{q}_1^- = S_{11} \cdot \underline{q}_{(k)}$ | 1: $\underline{q}_{(k)} \xrightarrow{Backscatter} \underline{q}_1^-$ |
| 2: $\underline{q}_1^+ = F \cdot (\underline{q}_1^-)^*$ | 2: $\underline{q}_1^- \xrightarrow{PCM} \underline{q}_1^+$ |
| 3: $\underline{q}_1^- = S_{11} \cdot \underline{q}_1^+$ | 3: $\underline{q}_1^+ \xrightarrow{Backscatter} \underline{q}_1^-$ |
| 4: $\underline{v} = F \cdot (\underline{q}_1^-)^*$ | 4: $\underline{q}_1^- \xrightarrow{PCM} \underline{v}$ |
| 5: $H_{k,k} = \underline{q}_{(k)}^H \cdot \underline{v}$ | 5: $H_{k,k} = \underline{q}_{(k)}^H \cdot \underline{v}$ |
| 6: $\underline{v} = \underline{v} - H_{k,k}\underline{q}_{(k)} - s_{(k-1)}\underline{q}_{(k-1)}$ | 6: $\underline{v} = \underline{v} - H_{k,k}\underline{q}_{(k)} - s_{(k-1)}\underline{q}_{(k-1)}$ |
| 7: $H_{k+1,k} = H_{k,k+1} = s_{(k)} = \|\underline{v}\|_2$ | 7: $H_{k+1,k} = H_{k,k+1} = s_{(k)} = \|\underline{v}\|_2$ |
| 8: $\underline{q}_{(k+1)} = \underline{v}/s_{(k)}$ | 8: $\underline{q}_{(k+1)} = \underline{v}/s_{(k)}$ |

From the Lanczos algorithm as implemented above, the matrix B may be determined using controller 224 as $$B = Q \cdot U \quad \text{Equation 27}$$

where $Q = [\underline{q}_{(1)} \ldots \hat{\underline{q}}_{(N_B)}]$ is the matrix with the modal coefficient vectors of the iterative wavefronts $\underline{q}_{(k)}$ as its columns and $U = [\underline{u}_{(1)} \ldots \underline{u}_{(N_B)}]$ is the matrix with the $N_B$ eigenvectors of matrix H associated with the $N_B$ smallest eigenvalues of matrix H as its columns. The convergence theory of the Lanczos algorithm predicts that the eigenvector estimates will rapidly converge to the K eigenvectors of $S_{11}^H \cdot S_{11}$ associated with the eigen-wavefronts of $S_{11}$ with the smallest reflection coefficients; hence, setting $N_B$ to be O(K) will suffice. The number of highly transmitting right eigenvectors K may be estimated by counting the number of eigenvalues of matrix H that are below a present level of $\in$. Therefore, the matrix B will be of dimensions $M \times K$, and the process described above for determining the amplitudes $p_l$ and the phases $\phi_l$ of the optimal focusing wavefront with modal coefficient vector $\underline{a}_{foc}$ may be accomplished using O(K) measurements.

Some or all calculations performed by the controller 224 in the embodiments described above (e.g., calculations for determining the modal coefficient vector associated with a wavefront or matrix-vector operations) may be performed by a computer such as a personal computer, laptop computer, server, mainframe, or specialized computing device or system. The calculations performed by the controller 224 may also be performed by a program or programs implemented on one or more computers. In some embodiments, some or all of the calculations may be performed by more than one computer communicatively connected through a network.

Figure 3:
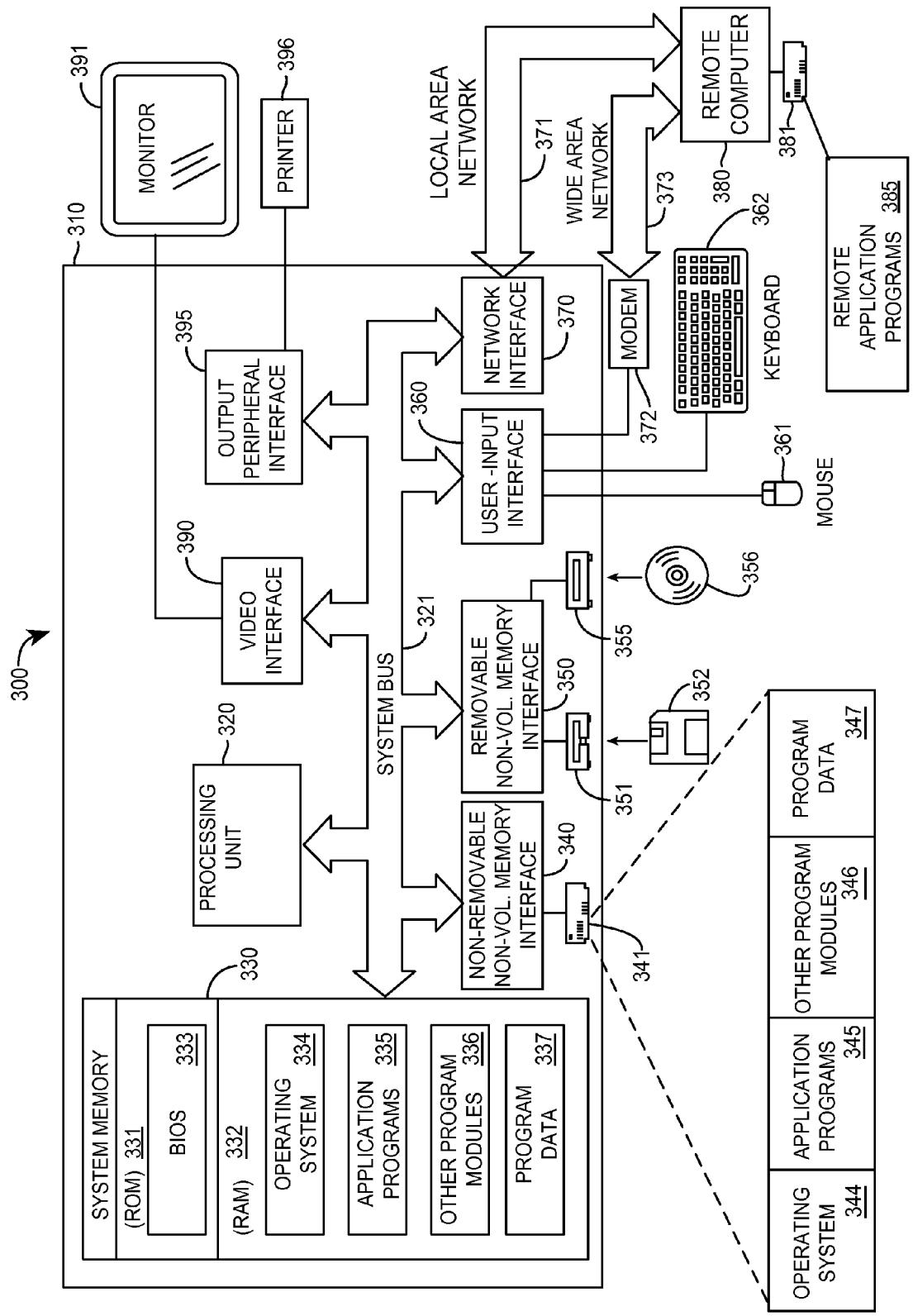
FIG. 3 illustrates an example computer system for implementing the methods for increasing transmission through a highly scattering random medium.

FIG. 3 illustrates an exemplary block diagram of a computer system 300 on which an exemplary method for increasing transmission through a highly scattering random medium may operate in accordance with the described embodiments. The computer system 300 of FIG. 3 includes a computing device in the form of a computer 310. Components of the computer 310 may include, but are not limited to, a processing unit 320, a system memory 330, and a system bus 321 that couples various system components including the system memory to the processing unit 320. The system bus 321 may be any of several types of bus structures including a memory bus or memory controller, a peripheral bus, and a local bus using any of a variety of bus architectures. By way of example, and not limitation, such architectures include the Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus (also known as Mezzanine bus).

Computer 310 typically includes a variety of computer readable media. Computer readable media can be any available media that can be accessed by computer 310 and includes both volatile and nonvolatile media, and both removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 310. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above are also included within the scope of computer readable media.

The system memory 330 includes computer storage media in the form of volatile and/or nonvolatile memory such as read only memory (ROM) 331 and random access memory (RAM) 332. A basic input/output system 333 (BIOS), containing the basic routines that help to transfer information between elements within computer 310, such as during start-up, is typically stored in ROM 331. RAM 332 typically contains data and/or program modules that are immediately accessible to and/or presently being operated on by processing unit 320. By way of example, and not limitation, FIG. 3 illustrates operating system 334, application programs 335, other program modules 336, and program data 337.

The computer 310 may also include other removable or non-removable, volatile or nonvolatile computer storage media. By way of example only, FIG. 3 illustrates a hard disk drive 341 that reads from or writes to non-removable, nonvolatile magnetic media, a magnetic disk drive 351 that reads from or writes to a removable, nonvolatile magnetic disk 352, and an optical disk drive 355 that reads from or writes to a removable, nonvolatile optical disk 356 such as a CD ROM or other optical media. Other removable or non-removable, volatile or nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 341 is typically connected to the system bus 321 through a non-removable memory interface such as interface 340, and magnetic disk drive 351 and optical disk drive 355 are typically connected to the system bus 321 by a removable memory interface, such as interface 350.

The drives and their associated computer storage media discussed above and illustrated in FIG. 3 provide storage of computer readable instructions, data structures, program modules and other data for the computer 310. In FIG. 3, for example, hard disk drive 341 is illustrated as storing operating system 344, application programs 345, other program modules 346, and program data 347. Note that these components can either be the same as or different from operating system 334, application programs 335, other program modules 336, and program data 337. Operating system 344, application programs 345, other program modules 346, and program data 347 are given different numbers here to illustrate that, at a minimum, they are different copies. A user may enter commands and information into the computer 310 through input devices such as a keyboard 362 and cursor control device 361, commonly referred to as a mouse, trackball or touch pad. A monitor 391 or other type of display device is also connected to the system bus 321 via an interface, such as a graphics controller 390. In addition to the monitor, computers may also include other peripheral output devices such as printer 396, which may be connected through an output peripheral interface 395.

The computer 310 may operate in a networked environment using logical connections to one or more remote computers, such as a remote computer 380. The remote computer 380 may be a personal computer, a server, a router, a network PC, a peer device or other common network node, and typically includes many or all of the elements described above relative to the computer 310, although only a memory storage device 381 has been illustrated in FIG. 3. The logical connections depicted in FIG. 3 include a local area network (LAN) 371 and a wide area network (WAN) 373, but may also include other networks.

When used in a LAN networking environment, the computer 310 is connected to the LAN 371 through a network interface or adapter 370. When used in a WAN networking environment, the computer 310 typically includes a modem 372 or other means for establishing communications over the WAN 373, such as the Internet. The modem 372, which may be internal or external, may be connected to the system bus 321 via the input interface 360, or other appropriate mechanism. In a networked environment, program modules depicted relative to the computer 310, or portions thereof, may be stored in the remote memory storage device 381. By way of example, and not limitation, FIG. 3 illustrates remote application programs 385 as residing on memory device 381.

The communications connections 370, 372 allow the device to communicate with other devices. The communications connections 370, 372 are an example of communication media. The communication media typically embodies computer readable instructions, data structures, program modules or other data in a modulated data signal such as a carrier wave or other transport mechanism and includes any information delivery media. A "modulated data signal" may be a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Computer readable media may include both storage media and communication media.

Throughout this specification, plural instances may implement components, operations, or structures described as a single instance. Although individual operations of one or more methods are illustrated and described as separate operations, one or more of the individual operations may be performed concurrently, and may, where appropriate, be performed in an order other than the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

What is claimed is:

1. A computer-implemented method for transmission of a wavefront through a medium, the computer-implemented method comprising:
    refining, with one or more processors, the wavefront in each of one or more iterations, including:
        transmitting, from a transmitter, a test wavefront into the medium;
        receiving, at a detector, a measurement of the back-scatter from the test wavefront entering the medium;
        determining, with one or more processors, whether the test wavefront achieves a numerically prespecified level of transmission through the medium based upon the received back-scatter;
        refining, with one or more processors, the test wavefront for transmitting into the medium in the next iteration based upon the received back-scatter;
    terminating the iterations when the numerically prespecified level of transmission through the medium is achieved;
    modifying, with one or more processors, the wavefront based upon the final test wavefront; and
    transmitting, from the transmitter, the modified wavefront through the medium.

2. The computer-implemented method of claim 1, wherein refining the test wavefront comprises one of the following: modifying the amplitude and phase of the test wavefront or modifying only the phase of the test wavefront.

3. The computer-implemented method of claim 1, wherein transmitting the test wavefront into the medium and receiving the measurement of the back-scatter from the test wavefront entering the medium in each of the one or more iterations comprises:

transmitting a first test wavefront into the medium;

receiving a measurement of a first backscatter wavefront from the first test wavefront entering the medium;

time-reversing the first backscatter wavefront to obtain a second test wavefront;

transmitting the second test wavefront into the medium;

receiving a measurement of a second backscatter wavefront from the second test wavefront entering the medium; and time-reversing the second backscatter wavefront to obtain a third test wavefront.

4. The computer-implemented method of claim 3, wherein refining the test wavefront for transmitting into the medium in the next iteration based upon the received back-scatter comprises adjusting the test wavefront in proportion to the third test wavefront and normalizing the adjusted test wavefront to have the same power as the wavefront.

5. The computer-implemented method of claim 3, wherein:

time-reversing the first backscatter wavefront to obtain a second test wavefront further comprises determining an average magnitude of the modal coefficients of the first backscatter wavefront, determining a phase-modulated first backscatter wavefront with the same modal coefficients as the first backscatter wavefront, and time-reversing the phase-modulated first backscatter wavefront; and refining the test wavefront for transmitting into the medium in the next iteration based upon the received back-scatter comprises adjusting the test wavefront in proportion to the product of the third test wavefront and the average magnitude of the modal coefficients of the first backscatter wavefront and determining a phase-modulated test wavefront with the same modal coefficients as the adjusted test wavefront.

6. The computer-implemented method of claim 3, wherein:

the first backscatter wavefront in each of the one or more iterations is distinct from the wavefront; and refining the test wavefront for transmitting into the medium in the next iteration based upon the received back-scatter comprises determining a residual vector from the third test wavefront.

7. The computer-implemented method of claim 3, wherein:

time-reversing the first backscatter wavefront to obtain a second test wavefront further comprises determining an average magnitude of the modal coefficients of the first backscatter wavefront, determining a phase-modulated first backscatter wavefront with the same modal coefficients as the first backscatter wavefront, and time-reversing the phase-modulated first backscatter wavefront; and refining the test wavefront for transmitting into the medium in the next iteration based upon the received back-scatter comprises adjusting the phase of the test wavefront in proportion to the average magnitude of the modal coefficients of the first backscatter wavefront.

8. The computer-implemented method of claim 3, wherein the time-reversing the first backscatter wavefront and the time-reversing the second backscatter wavefront are performed using a phase conjugate mirror.

9. The computer-implemented method of claim 3, wherein:

each of the one or more iterations further comprises determining one or more entries in a matrix H based upon the first test wavefront and the third test wavefront;

the computer-implemented method further comprises determining a matrix Q the columns of which are the modal coefficient vectors of the test wavefronts of each of the one or more iterations; and modifying the wavefront based upon the final test wavefront further comprises determining an optimal focusing wavefront based upon the matrix Q and the eigenvectors of the matrix H.

10. A system for transmission of a wavefront through a medium, the system comprising:

one or more processors;

one or more spatial light modulators configured to modulate the wavefront and transmit the modulated wavefront into the medium;

one or more detectors configured to measure the backscatter field resulting from the transmission of the wavefront into the medium; and a program memory storing non-transitory executable instructions that when executed by the one or more processors cause the system to:

refine the wavefront in each of one or more iterations, including:

causing the one or more spatial light modulators to transmit a test wavefront into the medium;

measuring, with the one or more detectors, the backscatter from the test wavefront entering the medium;

determining, with the one or more processors, whether the test wavefront achieves a numerically prespecified level of transmission through the medium based upon the received back-scatter;

refining, with the one or more processors, the test wavefront for transmitting into the medium in the next iteration based upon the received back-scatter;

terminate the iterations when the numerically prespecified level of transmission through the medium is achieved;

modify, with the spatial light modulator, the wavefront based upon the final test wavefront; and transmit, with the spatial light modulator, the modified wavefront through the medium.

11. The system of claim 10, further comprising executable instructions that when executed by the processor cause the system to refine the wavefront in each of the one or more iterations by causing the one or more spatial light modulators to transmit a test wavefront into the medium and measuring, with the one or more detectors, the back-scatter from the test wavefront entering the medium further comprises:

transmitting, with the spatial light modulator, a first test wavefront into the medium;

receiving a measurement of a first backscatter wavefront from the first test wavefront entering the medium;

time-reversing the first backscatter wavefront to obtain a second test wavefront;

transmitting the second test wavefront into the medium;

receiving a measurement of a second backscatter wavefront from the second test wavefront entering the medium; and time-reversing the second backscatter wavefront to obtain a third test wavefront.

12. The system of claim 10, wherein refining, with the one or more processors, the test wavefront for transmitting into the medium in the next iteration based upon the received back-scatter further comprises adjusting, with the one or more processors, the test wavefront in proportion to the third test wavefront and normalizing, with the one or more processors, the adjusted test wavefront to have the same power as the wavefront.

13. The system of claim 11, wherein:
the first backscatter wavefront in each of the one or more iterations is distinct from the wavefront; and
refining, with the one or more processors, the test wavefront for transmitting into the medium in the next iteration based upon the received back-scatter comprises determining, with the one or more processors, a residual vector from the third test wavefront.

14. The system of claim 11, further comprising one or more phase conjugate mirrors and wherein:
time-reversing the first backscatter wavefront to obtain a second test wavefront further comprises time-reversing, with the one or more phase conjugate mirrors, the first backscatter wavefront to obtain a second test wavefront; and
time-reversing the second backscatter wavefront to obtain a third test wavefront further comprises time-reversing, with the one or more phase conjugate mirrors, the second backscatter wavefront to obtain a third test wavefront.

15. A tangible, non-transitory computer-readable medium storing instructions for optimizing transmission of a wavefront through a medium that, when executed by one or more processors of a computer system, cause the computer system to:
refine the wavefront in each of one or more iterations, comprising:
causing a test wavefront to be transmitted into the medium;
receiving a measurement of the back-scatter from the test wavefront entering the medium;
determining whether the test wavefront achieves a numerically prespecified level of transmission through the medium based upon the received back-scatter;
refining the test wavefront for transmitting into the medium in the next iteration based upon the received back-scatter;
terminate the iterations when the numerically prespecified level of transmission through the medium is achieved;
cause the wavefront to be modified based upon the final test wavefront; and
cause the modified wavefront to be transmitted through the medium.

16. The tangible, non-transitory computer-readable medium of claim 15, wherein the executable instructions that when executed by the one or more processors cause the computer system to refine the wavefront in each of one or more iterations by causing a test wavefront to be transmitted into the medium and receiving a measurement of the back-scatter from the test wavefront entering the medium further comprise executable instructions that when executed by the one or more processors cause the computer system to refine the wavefront in each of one or more iterations by:
causing a first test wavefront to be transmitted into the medium;
receiving a measurement of a first backscatter wavefront from the first test wavefront entering the medium;
time-reversing the first backscatter wavefront to obtain a second test wavefront;
causing the second test wavefront to be transmitted into the medium;
receiving a measurement of a second backscatter wavefront from the second test wavefront entering the medium; and
time-reversing the second backscatter wavefront to obtain a third test wavefront.

17. The tangible, non-transitory computer-readable medium of claim 16, wherein:
refining the test wavefront for transmitting into the medium in the next iteration based upon the received back-scatter comprises adjusting the test wavefront in proportion to the third test wavefront and normalizing the adjusted test wavefront to have the same power as the wavefront; and
the time-reversing the first backscatter wavefront and the time-reversing the second backscatter wavefront are performed using a phase conjugate mirror.

18. The tangible, non-transitory computer-readable medium of claim 16, wherein:
time-reversing the first backscatter wavefront to obtain a second test wavefront further comprises determining an average magnitude of the modal coefficients of the first backscatter wavefront, determining a phase-modulated first backscatter wavefront with the same modal coefficients as the first backscatter wavefront, and time-reversing the phase-modulated first backscatter wavefront; and
refining the test wavefront for transmitting into the medium in the next iteration based upon the received back-scatter comprises adjusting the test wavefront in proportion to the product of the third test wavefront and the average magnitude of the modal coefficients of the first backscatter wavefront and determining a phase-modulated test wavefront with the same modal coefficients as the adjusted test wavefront.

19. The tangible, non-transitory computer-readable medium of claim 16, wherein:
time-reversing the first backscatter wavefront to obtain a second test wavefront further comprises determining an average magnitude of the modal coefficients of the first backscatter wavefront, determining a phase-modulated first backscatter wavefront with the same modal coefficients as the first backscatter wavefront, and time-reversing the phase-modulated first backscatter wavefront; and
refining the test wavefront for transmitting into the medium in the next iteration based upon the received back-scatter comprises adjusting the phase of the test wavefront in proportion to the average magnitude of the modal coefficients of the first backscatter wavefront.

20. The tangible, non-transitory computer-readable medium of 16, wherein the executable instructions that when executed by the one or more processors cause the computer system to refine the wavefront in each of one or more iterations further comprise executable instructions that when executed by the one or more processors cause the computer system to determine one or more entries in a matrix H based upon the first test wavefront and the third test wavefront, wherein the executable instructions that when executed by the one or more processors cause the computer system to determine a matrix Q the columns of which are the modal coefficient vectors of the test wavefronts of each of the one or more iterations, and wherein the executable instructions that when executed by the one or more processors cause the computer system to cause the wavefront to be modified based upon the final test wavefront further comprise executable instructions that when executed by the one or more processors cause the computer system to determine an optimal focusing wavefront based upon the matrix Q and the eigenvectors of the matrix H and modify the wavefront based upon the optimal focusing wavefront.

* * * * *